United States Patent
Bridger et al.

[11] Patent Number: 5,919,144
[45] Date of Patent: Jul. 6, 1999

[54] APPARATUS AND METHOD FOR MEASUREMENT OF INTRACRANIAL PRESSURE WITH LOWER FREQUENCIES OF ACOUSTIC SIGNAL

[75] Inventors: Keith Bridger, Washington, D.C.; Arthur V. Cooke, Baltimore, Md.; Frank J. Crowne, Laurel, Md.; Philip M. Kuhn, Severna Park, Md.; Joseph J. Lutian, Arnold, Md.; Edward J. Passaro, Towson, Md.; John M. Sewell, Cockeysville, Md.

[73] Assignee: Active Signal Technologies, Inc., Cockeysville, Md.

[21] Appl. No.: 08/851,796

[22] Filed: May 6, 1997

[51] Int. Cl.⁶ ......................................... A61B 5/00
[52] U.S. Cl. ............................. 600/561; 600/587
[58] Field of Search ................... 600/561, 559, 600/587, 451; 73/599, 602

[56] References Cited

U.S. PATENT DOCUMENTS

| | | | |
|---|---|---|---|
| 3,872,858 | 3/1975 | Hudson et al. | 128/2 V |
| 4,043,321 | 8/1977 | Soldner et al. | 128/2 V |
| 4,062,354 | 12/1977 | Taylor et al. | |
| 4,312,361 | 1/1982 | Nicholson et al. | 600/561 |
| 4,690,149 | 9/1987 | Ko | 128/653 |
| 4,819,648 | 4/1989 | Ko | 128/653 |
| 4,971,061 | 11/1990 | Kageyama et al. | 128/660.02 |
| 4,984,567 | 1/1991 | Kageyama et al. | 128/660.02 |
| 5,074,310 | 12/1991 | Mick | 600/561 |
| 5,117,835 | 6/1992 | Mick | 600/561 |
| 5,388,583 | 2/1995 | Ragauskas et al. | 128/661.05 |
| 5,411,028 | 5/1995 | Bonnefous | 128/661.08 |
| 5,617,873 | 4/1997 | Yost et al. | 128/748 |

FOREIGN PATENT DOCUMENTS

WO 9112767  9/1991  WIPO.

*Primary Examiner*—Marvin M. Lateef
*Assistant Examiner*—Ali M. Imam
*Attorney, Agent, or Firm*—Alan G. Towner; Eckert Seamans Cherin & Mellott, LLC

[57] ABSTRACT

A non-invasive apparatus and method are disclosed for measuring intracranial pressure. The intracranial measurement system transmits acoustic signals through a cranium and provides an indication of intracranial pressure based on the received acoustic signals after interaction with the brain. Properties such as acoustic transmission impedance, resonant frequency, resonance characteristics, velocity of sound and the like may be measured and correlated with intracranial pressure. The acoustic signals have typical frequencies of less than 100 kHz, for example, in the audible and sub-audible frequency ranges. The intensity of the transmitted acoustic signals used to determine intracranial pressure is relatively low, resulting in little or no health risks during short term or long term monitoring.

24 Claims, 3 Drawing Sheets

5,919,144

APPARATUS AND METHOD FOR MEASUREMENT OF INTRACRANIAL PRESSURE WITH LOWER FREQUENCIES OF ACOUSTIC SIGNAL

FIELD OF THE INVENTION

The present invention relates to the measurement of intracranial pressure, and more particularly relates to an apparatus and method for non-invasive measurement of intracranial pressure using acoustic signals.

BACKGROUND INFORMATION

The measurement of intracranial pressure (ICP) is important in diagnosing and treating various life threatening conditions caused by trauma, hemorrhage, tumors, inflammatory diseases and the like. Several techniques have been used to measure ICP. Conventional invasive ICP measurement techniques require a surgical passage through the skull bone into the ventricles, parenchyma or the region between the skull and dura mater to implant a measurement device.

A non-invasive ICP measurement technique has been suggested that determines distortions of the tympanic membrane of the ear. However, it has not been possible to obtain a good correlation with ICP because determination of ICP by this method is complicated by the compressible air space between the pressure source and the interrogation point.

Another non-invasive ICP measurement method measures the electro-magnetic impedance response of the brain to induced fields, and correlates the response to ICP. Such electro-magnetic measurement techniques are disclosed in U.S. Pat. Nos. 4,690,149 and 4,819,648 to Ko.

Another non-invasive ICP measurement technique that has been attempted involves ultrasonic imaging to detect relative displacements of tissue boundaries within the brain. The displacements may be associated with fluid build-up and compression or dilation of brain components, which permits determination of ICP through an independent calibration of compressibility. An alternate non-invasive ultrasonic technique involves the measurement of blood flow in the carotid artery by ultrasonic excitation of the artery and determination of Doppler frequency shift.

Various types of ultrasonic ICP measurement techniques are disclosed in U.S. Pat. Nos. 3,872,858 to Hudson et al., 4,043,321 to Soldner et al., 4,971,061 to Kageyama et al., 4,984,567 to Kageyama et al., 5,388,583 to Ragauskas et al. and 5,411,028 to Bonnefous. Such techniques involve the transmission of ultrasonic waves typically having frequencies on the order of 5 MHz into the cranium. A problem with ultrasonic excitation is the high intensities required in order to penetrate enough of the brain to sense the effect of increased ICP. Waves travelling through the intracranial region are absorbed at a substantially increasing rate as the frequency of the waves is increased. Ultrasonic frequencies on the order of 5 MHz require significant input power in order to produce usable signal-to-noise ratios. While ultrasonic input powers do not pose a health risk over relatively short time periods required for a typical clinical ultrasound scan, the FDA has limited cumulative exposure to 50 J/cm$^2$. A 100 W/cm$^2$ transducer utilizing one hundred 1 microsecond pulses every minute would exceed this limit in less than 100 hours. However, in some cases, patients may require continuous monitoring for at least a week. In addition, ultrasonic equipment is relatively large and expensive and is not suitable for field use or for dedicated monitoring of patients over long periods of time.

Each of the patents cited above is incorporated herein by reference.

Despite the above-noted attempts to develop ICP measurement techniques, no clinically useful devices are available and a need still exists for an ICP measurement apparatus and method which can measure ICP without skull penetration, which poses little or no health risks during long-term monitoring, and which is simple, compact and relatively inexpensive.

SUMMARY OF THE INVENTION

An object of the present invention is to provide an apparatus for measuring intracranial pressure including at least one acoustic signal transmitter for transmitting an acoustic signal into a cranium, at least one acoustic signal receiver for receiving the acoustic signal, and an analyzer for indicating intracranial pressure based on the received acoustic signal.

Another object of the present invention is to provide an apparatus for measuring intracranial pressure including means for transmitting an acoustic signal including frequencies of less than about 100 kHz into a cranium, and means for indicating intracranial pressure based on a driving point impedance of the acoustic signal transmitting means.

Another object of the present invention is to provide an apparatus for measuring intracranial pressure including means for measuring displacement of a cranium, and means for indicating intracranial pressure based on the measured displacement.

Another object of the present invention is to provide a method of measuring intracranial pressure including the steps of transmitting an acoustic signal into a cranium, receiving the acoustic signal from the cranium, and determining intracranial pressure from the acoustic response.

Another object of the present invention is to provide a method of measuring intracranial pressure including the steps of transmitting an acoustic signal including frequencies of less than about 100 kHz into a cranium with an acoustic signal transmitter, and indicating intracranial pressure based on a driving point impedance of the acoustic signal transmitter.

Another object of the present invention is to provide a method of measuring intracranial pressure including the steps of measuring a displacement of a cranium, and indicating intracranial pressure based on the measured displacement.

Another object of the present invention is to provide a method of measuring intracranial pressure including the steps of generating at least one resonant frequency within a cranium, and determining intracranial pressure based on the at least one resonant frequency.

These and other objects of the present invention will be more readily understood from the following description.

DETAILED DESCRIPTION OF THE PREFERRED EMBODIMENTS

The present invention provides an apparatus and method for non-invasive measurement of intracranial pressure. The system transmits acoustic signals through the cranium of a human or other mammal and provides an indication of ICP based on the properties of the received acoustic signals after interaction with the brain. Properties such as acoustic transmission impedance, velocity of sound, resonant frequency, resonance characteristics and the like may be measured and correlated with ICP.

The apparatus of the present invention comprises one or more acoustic signal transmitters and, in most instances, one or more acoustic signal receivers. The term "acoustic signal" as used herein includes signals having typical frequencies of less than about 100 kHz. The acoustic signal preferably includes frequencies of from 0 Hz to about 20 kHz, more preferably from about 1 Hz to about 10 kHz. A particularly preferred acoustic signal frequency range is from about 50 Hz to about 500 Hz. In accordance with an embodiment of the present invention, the frequency of the acoustic signal may approach or equal 0 Hz. In this embodiment, as the frequency approaches 0 Hz, the ICP measurement changes from an impedance or AC measurement to a displacement or static pressure measurement.

Figure 1:
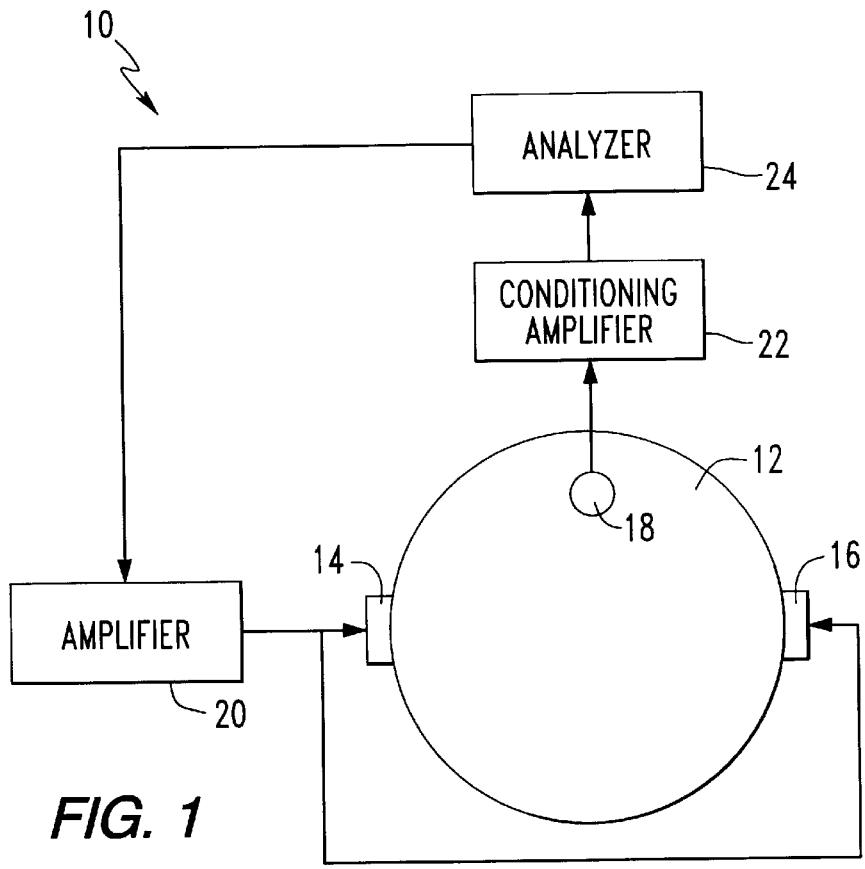
FIG. 1 is a schematic diagram illustrating an ICP measurement system in accordance with an embodiment of the present invention.

FIG. 1 schematically illustrates an ICP measurement system 10 in accordance with an embodiment of the present invention. The ICP of a subject's head 12 is measured by mounting acoustic signal transmitters 14 and 16 at the temples of the subject, or any other suitable location. An acoustic signal receiver 18 is mounted on the forehead of the subject, or at any other suitable position. A power amplifier 20 Such as a B&K Model 2706 amplifier provides electronic signals to the acoustic signal transmitters 14 and 16. A signal analyzer 24 such as a Hewlett-Packard HP3562A generates a signal to the power amplifier 20 which drives the acoustic signal transmitters 14 and 16. The brain is ensonified with these signals and the resulting signal after interaction with the brain is picked up by the sensor 18. The received signal may be conditioned and amplified by a conditioning amplifier 22 such as a B&K Model 2635 amplifier. The conditioning amplifier 22 may adjust the apparent impedance of the sensor 18 so that it can be read by the analyzer 24, and may also increase signal-to-noise ratio by filtering spurious signals. The signal is then acquired by the analyzer 24 for analysis according to power, frequency, impedance, etc. The analyzer 24 may display and/or record a trace corresponding to the acoustic signal received by the receiver 18. In a preferred embodiment, the analyzer 24 is integrated with the power amplifier 20 and can be used to compare the acoustic signals generated by the power amplifier 20 with the acoustic signals received by the receiver 18. The analyzer 24 may include a signal processing system having fast fourier transform (FFT), peak amplitude detection, and integrated energy calculation capabilities. A fast fourier transform provides the capability to take a given time segment of acoustic signal, for example the duration of a pulse or a scan, which has a variety of frequencies all mixed together and smeared over time, and determine the amplitude or amount of energy at each frequency. The frequency content or spectrum of the signal obtained by FFT may be used to characterize the acoustic response of the brain. The fourier transform is preferably carried out in close to real-time, such that the frequency content of a signal, averaged over very short time sequences, can be seen as it is being received.

The analyzer 24 may also include means for determining ICP based on the combination of data from the acoustic signal transmitters and receivers. In this embodiment, ICP is determined from analysis of the transmitted and received signals by examining the acoustic signature of the cranial response and subjecting this to mathematical analysis based on theoretical and empirical knowledge of the acoustic interaction with the brain. The acoustic signature is extracted from the signal by means such as FFT and conventional signal processing routines which are able to extract and quantify features such as resonant peaks and areas under given segments of curves. Typical acoustic analysis will include peak identification, peak height and sharpness or width at half peak height, resonant frequency, and area under the curve as a measure of total energy. Signal processing may be used to analyze the acoustic signal automatically and to increase signal-to-noise ratio based on algorithms established from a mathematical description of the physical and mechanical state of the brain, with emphasis on physical parameters and properties which interact most with an impinging acoustic wave. The most acoustically active elements in the brain are some of the fine structures within the cerebral vascular bed, such as the venules that lie between the large veins and the tiny capillaries. Mathematical analysis has shown that the viscous flow of blood into and out of these fine vascular structures in response to acoustic excitation will cause the unexpected low frequency resonances obtained in accordance with the present invention. Such low frequency resonant peaks may be attenuated by increasing ICP because the vascular structures are crushed to some extent by the brain pressure causing greater energy absorption in the viscous blood flow into and out of the vascular bed. The resonant peak height and/or area under the curve, both of which are indicators of attenuation, may be calibrated against ICP using this characteristic. Empirical calibration may come from the individual differences in head size and shape and skull thickness and vasculature which will cause differences in the location and height of the original peak corresponding to normal or close-to-zero ICP. By characterizing enough skull and people types, an indication of where the normal peak or attenuation level would be can be obtained. Alternatively, there may be combinations of parameters from the signal processing routines that will tie directly to the extent to which the vascular bed is crushed and hence read out ICP directly.

As more fully described below, the ICP measurement system 10 shown in FIG. 1 may be used to indicate changes in ICP, particularly increasing ICP, and to determine the actual ICP level. For example, broadband white noise over the range of 50–500 Hz may be generated by the power amplifier 20 and transmitted through the head 12 of the subject by means of the acoustic signal transmitters 14 and 16. The acoustic signals may then be picked up by the receiver 18 and transmitted to the conditioning amplifier 22. Acoustic signals of 50 millisecond duration may be repeated at intervals on the order of a few seconds to indicate whether there is any change in ICP. An indication of increasing ICP is an attenuation of the acoustic signals as the bursts or sweeps are repeated. Attenuation may be indicated by the results of the FFT on the acoustic signals, and comparison of earlier-received signal patterns with later-received patterns. Another indication of increasing ICP may be the shift in frequency, reduction or elimination of resonance peaks or appearance of new peaks in the signal patterns. In addition to changes in attenuation and resonance peaks, the ICP measurement system 10 may also analyze other parameters such as time of flight of the acoustic signal from one acoustic signal transmitter 14 to another acoustic signal transmitter 16 (acting in this case as a receiver), or to the acoustic signal receiver 18.

Other parameters such as pulsatile ICP and blood pressure of the subject may also be monitored. The ICP is typically not one value of pressure, but like blood pressure, has a maximum and a minimum cycling with about the same frequency (human pulse rate 45–150 cycles/min) as the blood pressure goes through its systolic and diastolic. Pulsing ICP may be observed over a short time span. The pulsatility of the ICP may be caused by the imposed fluctuating pressure of blood in the brain during the course of a blood pulse in the arteries. The amplitude of these ICP pulses (the height from maximum to minimum) relates closely to absolute ICP level. At high ICP the amplitude of ICP oscillation is higher. This type of effect may be measured with the present apparatus, and may be used as an element of the data reduction and analysis to arrive at an ICP from the measurements.

Furthermore, the bearing pressure of the acoustic signal transmitters 14 and 16 on the head 12 of the subject may be measured in accordance with the present invention by a suitable pressure sensor to indicate any pressure changes during the monitoring procedure. These various parameters may be weighted according to their shift or change with ICP in order to provide an indication of the change in ICP and/or the absolute value of ICP. In a preferred embodiment, the ICP measurement system indicates and displays both an ICP level and directions of recent change in ICP level, for example, at a patient's bedside monitor.

While two acoustic signal transmitters and one acoustic signal receiver are shown in FIG. 1, any suitable number of transmitters and receivers may be used. The transmitters and receivers may be mounted or attached to the head of a subject using a headband, helmet, or any other suitable means. Acoustic contact may be optimized by a coupling fluid for contact-type transmitters and receivers, or by a sealed air volume for air-coupled type transmitters and receivers.

The acoustic signal transmitters may be located at various positions on or near the head, preferably at locations where the parenchyma can be ensonified through the skull. The transmitters and receivers may also be placed in the same location or close vicinity of each other for compactness. Alternatively, one element alone can be used to transmit instantaneously and subsequently receive and then be repeatedly cycled in this way. Various types of acoustic signal transmitters may be used in accordance with the present invention, including direct contact, air-coupled and fluid-coupled transmitters. The acoustic signal transmitters may generate various types of signals including swept frequencies, multiple frequencies and single impulses. The transmitter may generate broadband white noise, pink noise, fixed sine waves, swept sine waves and the like, with broadband white noise being advantageous for many applications. The acoustic signal transmitters preferably operate at intensities of less than 10 mW/cm$^2$, preferably less than 1 mW/cm$^2$. During the intracranial pressure measurement process of the present invention, the cumulative exposure is preferably less than 50 J/cm$^2$, more preferably less than 10 J/cm$^2$.

In one embodiment, the acoustic signal transmitters may comprise cup-shaped headphones in which an internal electroacoustic transducer ensonifies a volume of air captured by a flexible perimeter seal, causing the head to form one wall of the captured volume. The sound in the captured air volume is thus coupled at various locations to the head and ensonifies the cranial cavity through the skull.

Alternatively, the acoustic signal transmitter may be of the contact type which directly ensonifies the skull and thereby the parenchyma. The interface between the contact transmitter and the skull preferably achieves maximum surface contact and maximum acoustic coupling to the skull.

Another type of acoustic signal transmitter is an electronically instrumented impulse hammer used to excite the brain through the skull. The impulse hammer sets up an acoustic signal in the brain with certain resonance frequencies. By measuring the impulse reaction force and acceleration, acoustical impedance can be determined. Other parameters such as sound speed or time of flight from the impulse to the receiver can be measured, providing a further indication of ICP. Techniques such as gating and/or cross correlation can be used for this measurement. In the gating method, reflections or spurious signals are gated out, by only looking at signals arriving within a given time window, so that the signal transmitted from the opposing exciter can be captured without interference. An oscilloscope can be used to perform this function. Another technique is the use of cross correlation whereby the recorded transmit signal is compared with the first received signal and the time of maximum peak is recorded as the time of flight. This function is a standard function available on analyzers such as the HP3562.

In another embodiment, the acoustic signal transmitter also serves as the acoustic signal receiver. In this embodiment, the driving point impedance of an active transducer is measured. At the temple location, the skull is relatively thin such that determination of the parenchymal properties are least effected by the skull. For a low ICP which makes the head appear relatively soft to the impinging transducer, the velocity of the active transducer head is relatively high. For an electroactive ceramic device such as PZT, the high transducer velocity generates relatively high current and low voltage, resulting in a low impedance value. For a high ICP which makes the head appear relatively hard to the transducer, the velocity of the active transducer head is relatively low. In this case, the transducer head generates a low current and high voltage, resulting in a relatively high impedance value. The converse is true if the transducer is of the magnetic type. Thus, the driving point impedance value of the active transducer provides an indication of ICP inasmuch as it is also an indication of reduction of sharpness of resonance, or reduced attenuation. In this embodiment, a current monitor is coupled to the driving circuit along with the voltage monitor. The relationship of the current and voltage as a function of frequency are then monitored to generate values of real and/or imaginary parts of the impedance. The real part of the impedance will be the most likely indicator of ICP in that it is the closest correlate to the attenuation of the signal which is a typical result of increasing ICP.

In accordance with another embodiment, the acoustic signal transmitter may use a localized fluid filled calibrated pressure mini chamber attached to the skull in which small increases in ICP couple to the fluid in the chamber such that the chamber pressure is increased. As ICP increases, the pressure bearing against the inside of the skull at any point becomes greater. For a thin part of the skull, such as the temples, this pressure causes two effects, both of which can be measured. The first is an actual outward extension of the skull itself to which can be measured with a very fine caliper or a fluid-filled cavity. If the cavity has a flexible window bearing against the skull where it bows out then an increase in pressure can be registered within the oil using a conventional immersion pressure gauge corresponding to the increased ICP. The second effect of the higher internal pressure is to cause the effective stiffness of the skull to increase. This stiffness can be determined by a rapid stress-strain measurement on the skull at that point by pumping up the pressure in the oil-filled chamber so that the flexible end exerts a force locally on the skull. The less added volume of fluid it takes to cause a given pressure rise in the chamber, the stiffer the skull. Alternatively, the amount of pressure needed to be applied to cause a certain amount of skull movement expressed as a stress-strain curve gives the effective stiffness of the skull. While this is one embodiment for 0 Hz or static pressure measurement, other types of displacement measurements may be made in accordance with the present invention.

Figure 2:
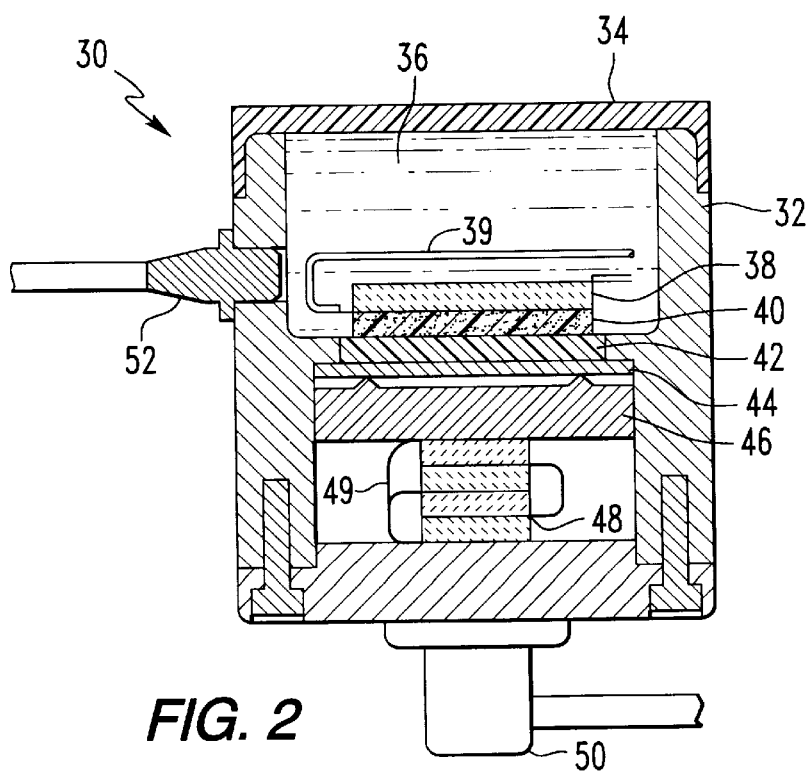
FIG. 2 is a partially schematic sectional drawing of an acoustic signal transmitter in accordance with an embodiment of the present invention.

FIG. 2 is a partially schematic sectional drawing of an acoustic signal transmitter 30 in accordance with an embodiment of the present invention. The acoustic signal transmitter 30 includes a housing 32 made of any suitable material such as aluminum. A window 34 made of polyurethane or similar type of material that is substantially acoustically transparent covers an end of the housing 32. The housing 32 and window 34 form a cavity 36 which may be filled with fluid such as low viscosity oil. The fluid inside the cavity 36 preferably has substantially the same acoustic impedance as water.

A piezoelectric sensor 38 is optionally mounted within the cavity 36 on a syntactic foam backing 40 or other acoustic reflecting material. The sensor 38 preferably comprises a piezoelectric material such as lead zirconate titanate (PZT). A suitable piezoelectric material is commercially available under the designation PZT 4. Electrical contacts 39 are made on opposing planar sides of the piezoelectric sensor 38. In a known manner, acoustic waves impinging on the piezoelectric sensor 38 are converted into electrical signals.

A coupling window 42 made of a substantially acoustically transparent material such as polyurethane divides the housing 32. The coupling window 42 acts as both a sealer and a substantially acoustically transparent interface to couple the energy from the actuator 48 through the fluid in the cavity 36 to the cranium without substantial loss. A diaphragm 44 made of steel contacts the coupling window 42. A piston 46 made of aluminum contacts the diaphragm 44 by means of a raised annular ring. The piston 46 is secured to an actuator 48, preferably made of piezoelectric material such as PZT 4.

As shown in FIG. 2, the actuator 48 preferably comprises a stack of piezoelectric elements. Electrical contacts 49 are located on opposing planar surfaces of the piezoelectric elements. In a known manner, the provision of an electrical signal to the piezoelectric actuator 48 by means of the electrical contacts 49 causes displacement of the actuator in a longitudinal direction. The displacement causes the piston 46 and diaphragm 44 to vibrate. The vibration or acoustic signal is transmitted through the coupling window 42, fluid filled cavity 36 and window 34.

As shown in FIG. 2, a connector 50 is attached to a backing plate secured to the housing 32. The connector 50 allows for electrical connection to the contacts 39 and 49, and also serves to internally ground and shield the housing, 32.

The acoustic signal transmitter 30 may optionally include a pressure transducer 52. The pressure transducer 52 may be used to pick up pressure variations within the fluid filled cavity 36. The pressure transducer 52 preferably has a high frequency response and is capable of sensing pressure variations ranging from 0 to 100 kHz, more preferably from 0 Hz to 1 kHz. The pressure transducer 52 may be used to measure steady-state pressure within the cavity 36. Increasing pressure levels within the cavity 36 provide an indication of increasing ICP in accordance with an embodiment of the present invention. The pressure transducer 52 may also be used to sense higher frequency pressure changes as a function of the stiffness of the interface between the window 34 and the cranium. In accordance with an embodiment of the present invention, such increasing stiffness provides an indication of increasing ICP.

The acoustic signal receivers of the present invention are preferably placed in contact with the head at any suitable location which allows sensing of the acoustic signal produced in the parenchyma. In a preferred embodiment, a single acoustic signal receiver is centrally located on a subject high on the forehead above the sinus cavities. The acoustic signal receiver may generate an electrical signal indicative of ICP by means of a sensor which picks up the acoustic signal transmitted through the cranium, or by measurement of current or voltage through an active transducer. The acoustic signal receivers may be of any suitable type such as piezoelectric sensors, micro electromechanical sensors, piezoelectric polymers, magnetic films, moving coil type and geophones, with piezoelectric sensors being preferred for many applications. Particularly suitable receivers comprise active sensing elements such as piezoelectric ceramics incorporated into mechanical designs that amplify the magnitude of the received displacement at the expense of some force. An example is the Morgan Matroc Adrenal Pressure Sensor which consists of a piezoelectric bimorph, comprising two extremely thin piezoelectric plates mounted on either side of a fine brass vane, in the form of a narrow ribbon mounted in a metal housing with lever mechanisms to increase the displacement amplitude received at the bimorph. Where the acoustic signal approaches or equals 0 Hz, suitable receivers include strain gauges, piezoelectric pressure and displacement sensors.

Active or passive acoustic signal receivers may be used. While the sensors are used passively, they simply listen to the activity of the brain or sense pressure waves or displacements naturally emanating from the brain. In this mode, there is no input signal and the ICP is derived from the physiological pulsatile activity of the brain. This can be manifest as an effect of ICP on arterial pressure or change in amplitude of oscillation of the ICP itself. In the active mode, the sensors measure the effect of positive pressure, either DC or AC signals, applied to the brain.

The electrical signal generated by the acoustic signal receiver may be processed using any suitable frequency or time domain analysis. The signal can be analyzed for transmission losses and/or resonances. The sensed acoustic signal includes many parameters which may be analyzed and correlated with ICP. Such parameters include peak height, peak sharpness or Q value determined by the width of a peak at half of its height, specific frequencies, frequency shifts, peak height shifts, and integrated energy determined by the area under the sensor trace. The various parameters of the sensed acoustic signal may be compared with a baseline signal for a given patient, or may be compared with a baseline signal common to a particular group of people. Furthermore, the ICP pressure measurement apparatus and method of the present invention permits continuous or periodic monitoring of ICP changes of a patient in various situations such as emergency rescue, military and surgical operations.

Absolute ICP and change in ICP measurements may require differences in the level of processing and database applied to the signal. A field emergency device to remain portable might not carry on-board signal processing capability and an extensive library of look-up tables needed to derive an absolute ICP value. Instead it might look for simple shifts in distribution on the FFT or frequency shifts or attenuation or changes in area under portions of the curve. These could indicate change, which in itself is indicative of problems since a healthy person has a stable ICP. The change recorder can also be used to sense a steady high value of ICP that is not changing in the following manner. If a head injured patient is suspected of having elevated ICP, but shows no response on the change monitor, it is possible to administer certain treatments that are known to lower elevated ICP and yet be fairly benign to the patient even if there is no ICP problem. If at the point these drugs, such as mannitol and hypertonic saline, are administered, the change monitor indicates a decreasing ICP level, this is an indication that the ICP was at a steady high level at the outset.

The following examples are intended to illustrate various aspects of the present invention, and are not intended to limit the scope thereof.

EXAMPLE 1

ICP measurements were made on subjects oriented in various positions. Measurements were made on each subject in an upright standing or sitting position, in a supine position, and in a head-down inclined position at −45 degrees. The set-up for ICP pressure measurement included a seesaw used to change the height of the head relative to the center of the body and thereby simulate elevated ICP conditions. A headset including acoustic signal transmitters and an acoustic signal receiver similar to that shown in FIG. 1 was used. An amplifier and signal generator, which may optionally be part of the acquisition equipment, were used to generate an acoustic signal. An acquisition system was used to record the sensed acoustic signal, and to display the variations in the acoustic signal resulting from differing ICP. The acoustic signal transmitters and receiver were mounted on each subject's head using a headset consisting of a band which held each transmitter over the ear or on the temple of each subject and positioned the receiver at the upper forehead of each subject. Three different types of acoustic signal transmitters were used. Earphones placed over the ears comprised conventional stereo headphones having electroacoustic transducers. RD actuators placed on the temples comprised commercially available miniature electrodynamic shakers. Baynesville actuators placed on the temples comprised commercially available 1 inch electrodynamic loudspeaker elements. The acoustic signal receiver, which was centrally located high on the forehead of each subject above the sinus cavities, comprised a Morgan Matroc Adrenal Pressure Sensor. A B&K Model 2706 power amplifier was used to drive the acoustic signal transmitters, while an analyzer or acquisition system was used to provide the appropriate signal to the power amplifier and acquire data from the sensor. The acquisition system comprised a Hewlett-Packard Model HP3562A connected to a B&K Model 2635 conditioning amplifier. The acoustic signal transmitters were driven over a range of from 1 Hz to 20 kHz with a swept sine wave to ensonify the cranium through the ear canals using headphones or through the temples using the speakers or actuators. The frequency range of 10 to 1,000 Hz yielded particularly useful resonance and attenuation data. A relatively low acoustic signal amplitude of about 80 dBA was used. The acoustic signal transmitters were excited at the same time in parallel. The resonance and attenuation of the acoustic signals for each subject in various positions are shown below in Table 1.

TABLE 1

| Subject No. | Position | Actuator | Resonance (Hz) | Attenuation (dB) |
|---|---|---|---|---|
| 1 | upright | earphone | 230 | −27 |
| 1 | supine | earphone | 260 | −43 |
| 1 | head-down inclined | earphone | none | −60 |
| 2 | upright | earphone | 230 | −40 |
| 2 | head-down inclined | earphone | none | −75 |
| 2 | upright | RD actuator | 492 | −6.2 |
| 2 | supine | RD actuator | 578 | −8.7 |
| 2 | head-down inclined | RD actuator | 428 | −14.9 |
| 3 | upright | Baynesville speaker | 344 | −24.2 |
| 3 | supine | Baynesville speaker | 365 | −26.8 |
| 3 | head-down inclined | Baynesville speaker | 365 | −29.4 |
| 3 | upright | earphone | 367 | −55 |
| 3 | supine | earphone | 367 | −57 |
| 3 | head-down inclined | earphone | none | −62.4 |

EXAMPLE 2

Figure 3:
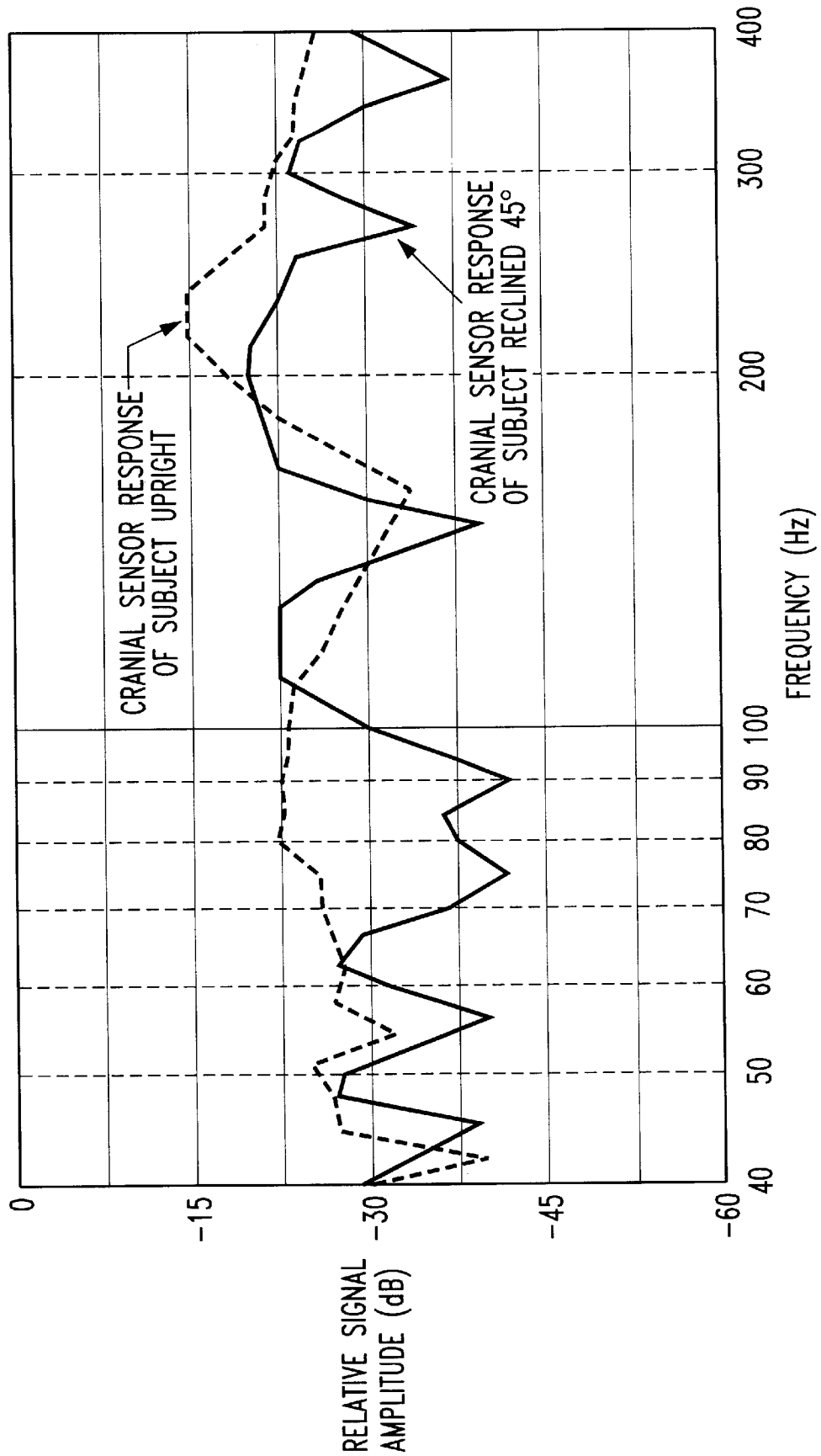
FIG. 3 is a graph showing intracranial acoustic response for a subject in an upright position and in a head-down inclined position. The acoustic signal resonant peak is attenuated when the subject is in the head-down inclined position, reflecting an increase in ICP.

Intracranial pressure of a subject was measured using an apparatus and procedure similar to that of Example 1, except the acoustic signal receiver comprised a conventional accelerometer modified with a mechanical amplifier. The accelerometer was mounted in a housing and was connected to a piston and diaphragm assembly similar to that shown in FIG. 2 which served as a mechanical amplifier. Acoustic signals entering an air-filled cavity of the housing were amplified by the piston and diaphragm assembly prior to impingement with the accelerometer. Using a set-up similar to that described in Example 1, the ICP of the subject was alternately measured in an upright position and a head-down inclined position. FIG. 3 is a graph showing the difference in acoustic signal attenuation for the subject in the upright position and in the head-down inclined position. A substantial decrease in signal amplitude is demonstrated at a frequency of between 200–300 Hz for the subject in the head-down inclined position versus the upright position, indicating an increase in ICP. In FIG. 3, the response of the upper trace, where the subject was upright, shows a resonance at 232 Hz and a signal level of −14 dBV. When the subject was head-down inclined at an angle of −45 degrees, as shown in the lower trace, the resonance is damped and the acoustic signal is substantially attenuated in the frequency range of about 100 to 500 Hz. In addition to changes in resonance and attenuation, other parameters such as time of flight and acoustic impedance may be used to determine ICP in accordance with the present invention.

EXAMPLE 3

Figure 4:
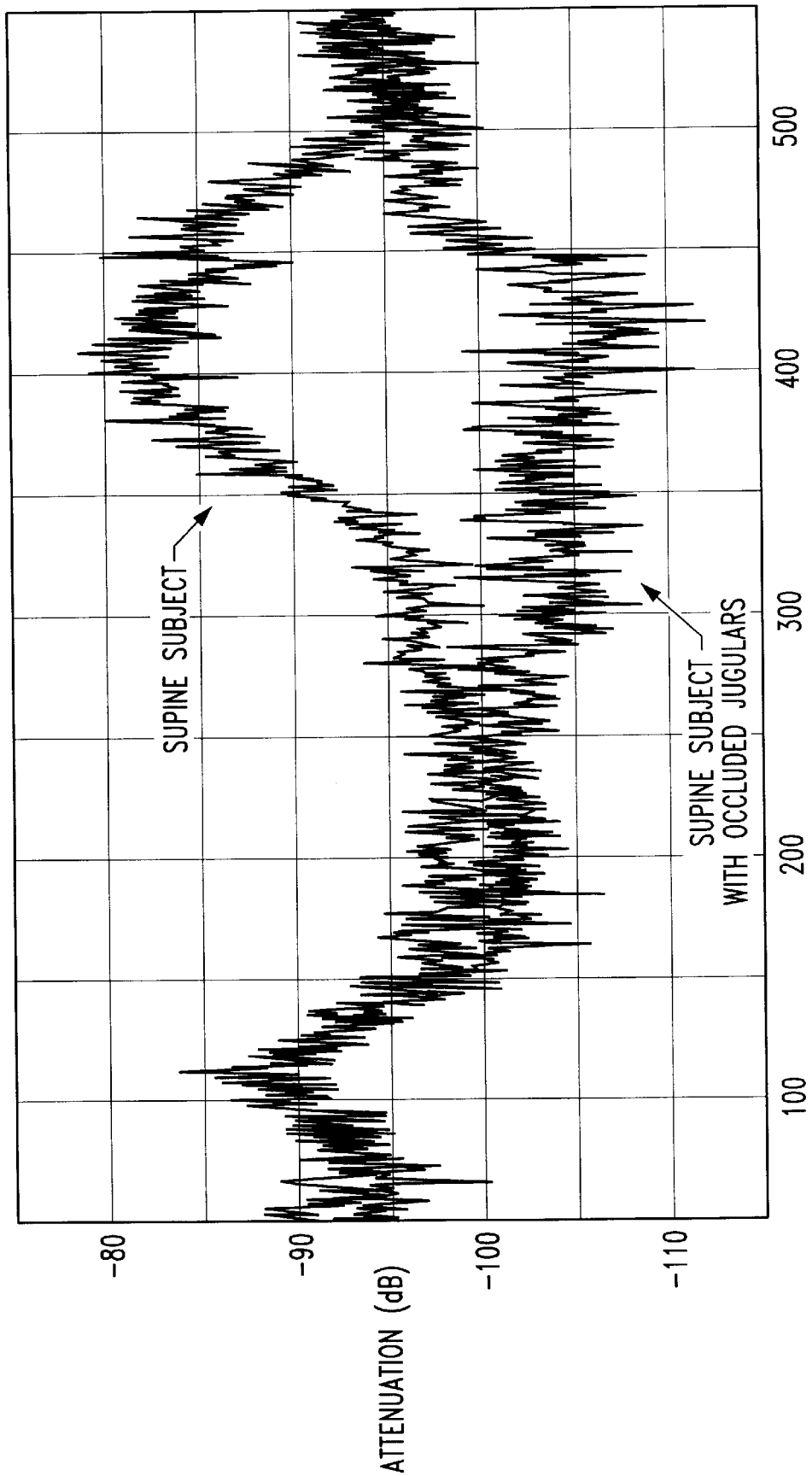
FIG. 4 is a graph showing the intracranial acoustic response of a supine subject in a normal condition and with occluded jugulars. The blocking of the jugulars and the resultant increase in ICP results in attenuation of the acoustic signal.

Intracranial pressure of a supine subject was measured with the subject in a normal condition and with the jugular veins of the subject occluded. The measurement system was similar to that shown in FIG. 1 and described in Example 1, with the acoustic signal transmitters comprising RD actuators in the form of miniature electrodynamic shakers. The signal to the subject's head was a burst of white noise in the frequency range of 50–500 Hz produced by a Hewlett- Packard HP3562 as a signal generator and a B&K 2706 power amplifier. Occlusion of the subject's jugulars resulted in increased ICP, which was measured as a substantial attenuation of the acoustic signal in the frequency range of 250–500 Hz. The attenuation due to increased ICP is shown in FIG. 4.

The apparatus and method of the present invention possess several advantages over conventional ICP measurement techniques. The present system is non-invasive and is very sensitive to ICP. The intensity of the transmitted acoustic signals used to determine ICP in accordance with the present invention is relatively low, resulting in little or no health risks during long term monitoring. The apparatus is simple, compact and relatively inexpensive, making the system suitable for use in the field as well as in hospitals and the like. In accordance with the present invention, ICP may be measured during various types of procedures by surgeons, EMS personnel, triage personnel, etc.

While particular embodiments of the present invention have been described herein, it is to be understood that various changes, modifications, additions and adaptations are within the scope of the present invention, as set forth in the following claims.

What is claimed is:

1. Apparatus for measuring intracranial pressure comprising:
    at least one acoustic signal transmitter capable of transmitting an acoustic signal including frequencies of less than about 100 kHz into a cranium to ensonify a brain in the cranium;
    at least one acoustic signal receiver in communication with the acoustic signal transmitter for receiving the acoustic signal; and
    an analyzer capable of indicating intracranial pressure based on the received acoustic signal.

2. The apparatus of claim 1, wherein the acoustic signal includes frequencies of from 0 Hz to about 20 kHz.

3. The apparatus of claim 1, wherein the acoustic signal includes frequencies of from about 1 Hz to about 10 kHz.

4. The apparatus of claim 1, wherein the acoustic signal includes frequencies of from about 50 Hz to about 500 Hz.

5. The apparatus of claim 1, further comprising a power amplifier connected to the at least one acoustic signal transmitter.

6. The apparatus of claim 1, further comprising a conditioning amplifier connected between the at least one acoustic signal receiver and the analyzer.

7. The apparatus of claim 1, wherein the analyzer includes means for determining an attenuation of the received acoustic signal, a change in resonance of the received acoustic signal, a shift in peak resonant frequency of the received acoustic signal, a change in driving point impedance of the at least one acoustic signal transmitter, a change in velocity of the acoustic signal, or a combination thereof.

8. Apparatus for measuring intracranial pressure comprising:
    means for transmitting an acoustic signal including frequencies of less than about 100 kHz into a cranium to ensonify a brain in the cranium;
    means for receiving the acoustic signal; and
    means for indicating intracranial pressure based on the received acoustic signal.

9. The apparatus of claim 8, wherein the acoustic signal includes frequencies of from 0 Hz to about 20 kHz.

10. The apparatus of claim 8, wherein the acoustic signal includes frequencies of from about 1 Hz to about 10 kHz.

11. The apparatus of claim 8, wherein the acoustic signal includes frequencies of from about 50 Hz to about 500 Hz.

12. The apparatus of claim 11, wherein the intracranial pressure indicating means includes means for determining an attenuation of the received acoustic signal, a change in resonance of the received acoustic signal, a shift in peak resonant frequency of the received acoustic signal, a change in driving point impedance of the acoustic signal transmitting means, a change in velocity of the acoustic signal, or a combination thereof.

13. Apparatus for measuring intracranial pressure comprising:
    means for transmitting an acoustic signal including frequencies of less than about 100 kHz into a cranium; and
    means for indicating intracranial pressure based on a driving point impedance of the acoustic signal transmitting means.

14. A method of measuring intracranial pressure comprising:
    receiving an acoustic signal including frequencies of less than about 100 kHz from an ensonified brain in a cranium; and
    determining intracranial pressure from the received acoustic signal.

15. The method of claim 14, further comprising transmitting the acoustic signal into the cranium.

16. The method of claim 15, wherein the acoustic signal includes frequencies of from 0 Hz to about 20 kHz.

17. The method of claim 15, wherein the acoustic signal includes frequencies of from about 1 Hz to about 10 kHz.

18. The method of claim 15, wherein the acoustic signal includes frequencies of from about 50 Hz to about 500 Hz.

19. The method of claim 15, further comprising:
    mounting at least one acoustic signal transmitter on the cranium of a subject; and
    activating the at least one acoustic signal transmitter to transmit the acoustic signal into the cranium.

20. The method of claim 19, further comprising:
    mounting at least one acoustic signal receiver on the cranium of the subject; and
    receiving the acoustic signal with the acoustic signal receiver.

21. The method of claim 15, wherein the intracranial pressure is determined by an attenuation of the received acoustic signal, a change in resonance of the received acoustic signal, a shift in a peak resonant frequency of the received acoustic signal, a change in driving point impedance of an acoustic signal transmitter, a change in velocity of the acoustic signal, or a combination thereof.

22. A method of measuring intracranial pressure comprising:
    transmitting an acoustic signal including frequencies of less than about 100 kHz into a cranium with an acoustic signal transmitter; and
    indicating intracranial pressure based on a driving point impedance of the acoustic signal transmitter.

23. A method of measuring intracranial pressure comprising:
    generating at least one resonant frequency within a brain in a cranium; and
    determining intracranial pressure based on the at least one resonant frequency.

24. The method of claim 23, wherein the intracranial pressure is determined by an attenuation of the at least one resonant frequency, a shift of the at least one resonant frequency, or a combination thereof.

* * * * *

UNITED STATES PATENT AND TRADEMARK OFFICE
CERTIFICATE OF CORRECTION

PATENT NO. : 5,919,144
DATED : July 6, 1999
INVENTOR(S) : Keith Bridger, et al.

It is certified that error appears in the above-identified patent and that said Letters Patent is hereby corrected as shown below:

Col. 6, line 66 delete the word "to" after "itself"

Col 8, line 41 "While" should read -- When --

Col. 10, Table 1, 1st line under column titled "Attenuation (dB)" "-27" should read -- -37 --

Col. 10, Table 1, after line 4, a line was omitted and should read

| Subject No. | Position | Actuator | Resonance (Hz) | Attenuation (dB) |
|---|---|---|---|---|
| 2 | supine | earphone | none | -65 |

Signed and Sealed this

Twenty-eighth Day of November, 2000

Attest:

Q. TODD DICKINSON

Attesting Officer

Director of Patents and Trademarks